(12) United States Patent
Chen

(10) Patent No.: US 11,059,020 B2
(45) Date of Patent: Jul. 13, 2021

(54) ELECTRONIC WASTE PROCESSING METHOD AND APPARATUS THEREOF

(71) Applicants: Hsuan-Jung Chen, Yunlin County (TW); JING LEEI ENTERPRISE CO., LTD., Kaohsiung (TW)

(72) Inventor: Hsuan-Jung Chen, Yunlin County (TW)

(73) Assignees: Hsuan-Jung Chen, Yunlin County (TW); JING LEEI ENTERPRISE CO., LTD., Kaohsiung (TW)

( * ) Notice: Subject to any disclaimer, the term of this patent is extended or adjusted under 35 U.S.C. 154(b) by 437 days.

(21) Appl. No.: 16/253,894

(22) Filed: Jan. 22, 2019

(65) Prior Publication Data

US 2020/0030815 A1   Jan. 30, 2020

(30) Foreign Application Priority Data

Jul. 24, 2018   (TW) .................................. 107125464

(51) Int. Cl.
| | |
|---|---|
| *B01J 19/12* | (2006.01) |
| *B03B 9/06* | (2006.01) |
| *A61L 11/00* | (2006.01) |
| *C10B 47/02* | (2006.01) |
| *C10K 1/04* | (2006.01) |
| *C10B 19/00* | (2006.01) |
| *C10B 57/04* | (2006.01) |

(Continued)

(52) U.S. Cl.
CPC .............. *B01J 19/12* (2013.01); *A61L 11/00* (2013.01); *B03B 9/061* (2013.01); *C10B 19/00* (2013.01); *C10B 47/02* (2013.01); *C10B 53/07* (2013.01); *C10B 57/04* (2013.01); *C10G 1/10* (2013.01); *C10K 1/024* (2013.01); *C10K 1/04* (2013.01); *B09B 3/00* (2013.01); *B09B 3/0083* (2013.01); *C10B 1/02* (2013.01); *C10G 2300/1003* (2013.01); *C22B 7/005* (2013.01)

(58) Field of Classification Search
None
See application file for complete search history.

(56) References Cited

U.S. PATENT DOCUMENTS

2009/0000938 A1* 1/2009 Kasin ...................... C10B 19/00
                                                                201/2.5

FOREIGN PATENT DOCUMENTS

| CN | 101423898 A | 5/2009 |
|---|---|---|
| CN | 103320618 A | 9/2013 |

(Continued)

*Primary Examiner* — Derek N Mueller
(74) *Attorney, Agent, or Firm* — Rabin & Berdo, P.C.

(57) ABSTRACT

An electronic waste processing apparatus has a power supply device, a vacuum cracking device, a filter device, and a separation device. The vacuum device is electrically connected to the power supply device, and has a vacuum pump, a vacuum chamber, and a high-frequency furnace body. The vacuum chamber is connected to and communicates with the vacuum pump. The high-frequency furnace body is disposed in the vacuum chamber. The filter device is electrically connected to the power supply device, and is connected to and communicates with the high-frequency furnace body of the vacuum cracking device. The separation device is electrically connected to the power supply device, is connected to and communicates with the vacuum pump and the filter device, and has a condensation cylinder, a cooling cylinder, and an oil storage tank.

20 Claims, 6 Drawing Sheets

(51) Int. Cl.
*C10G 1/10* (2006.01)
*C10K 1/02* (2006.01)
*C10B 53/07* (2006.01)
C22B 7/00 (2006.01)
B09B 3/00 (2006.01)
C10B 1/02 (2006.01)

(56) References Cited

FOREIGN PATENT DOCUMENTS

| | | |
|---|---|---|
| CN | 104384168 A | 3/2015 |
| CN | 104624611 A | 5/2015 |
| CN | 107866437 A | 4/2018 |
| TW | I268184 B | 12/2006 |
| TW | M569255 U | 11/2018 |

* cited by examiner

… (US 11,059,020 B2)

ELECTRONIC WASTE PROCESSING METHOD AND APPARATUS THEREOF

BACKGROUND OF THE INVENTION

1. Field of the Invention

The present invention relates to an electronic waste processing method and apparatus thereof, and more particularly relates to an electronic waste processing method and apparatus thereof that may be used safely and environmentally friendly, with the electronic waste fully recycled.

2. Description of Related Art

Due to the rapid development of science and technology and the rapid changes in society, the use of electronic products is closely related to people's lives. However, due to the widespread and extensive use of electronic products, the discarded parts, circuit boards or circuit accessories of the electronic products increase year by year. At present, the electronic waste is mainly discarded by high temperature (about 1500° C.) combustion in a furnace body. The electronic waste placed in the furnace body is subjected to high temperature. During the combustion treatment, in which the electronic waste includes plastic materials and metal materials at the same time, the plastic materials will generate toxic gas such as dioxin in the process of high temperature combustion, and must be processed by an air pollution treatment device for treating the harmful gas and to avoid pollution to the environment.

The conventional high-temperature combustion treatment method and device can treat the electronic waste, but in the process of high-temperature combustion, gas such as hydrogen chloride (HCl) is generated, and the hydrogen chloride gas is generated in a combustion device such as the furnace body. Instantaneous high pressure is generated, which makes the furnace body or the combustion device tend to generate a gas explosion during the high-temperature combustion process, and relatively increases the safety concerns in use. Furthermore, the toxic gas generated during the combustion process must be provided with an air pollution equipment to provide a filtration and disinfection effect, relatively increasing the cost of use and having an impact on the health of the field operators. Additionally, the increased equipment and required power are not environmentally friendly. In addition, the toxic gases and residues generated after high temperature combustion can no longer be used, which limits the practicality of the electronic waste. In view of the above, the conventional method and device for high-temperature combustion of the electronic waste need to be improved.

To overcome the shortcomings, the present invention provides an electronic waste processing method and apparatus thereof to mitigate or obviate the aforementioned problems.

SUMMARY OF THE INVENTION

The main objective of the present invention is to provide an electronic waste processing method and apparatus thereof that may be used safely and environmentally friendly, with the electronic waste fully recycled.

The electronic waste processing method in accordance with the present invention has a preparation step, a vacuum cracking step, a recovery step, a separation step, and a subsequent processing step. In the preparation step, electronic waste, a power supply device, a vacuum cracking device, a filter device, and a separation device are prepared. In the vacuum cracking step, the electronic waste is sent to the vacuum cracking device. The vacuum pump is driven by the power supply device and is connected to the vacuum chamber, and this enables an interior of the vacuum chamber to be in a vacuum state via the vacuum pump and the power supply device. The high-frequency furnace body is disposed in the vacuum chamber and is supplied with power required for high-frequency heating from the power supply device. In the recovery step, gaseous oil and gas and liquid metal generated in the vacuum cracking step are recovered.

In the separation step, the filtered gaseous oil and gas is pipelined to the separation device. After the filtered gaseous oil and gas is cooled in the condensation cylinder of the separation device, a portion of the filtered gaseous oil and gas generates liquid oil and is stored therein. The oil storage tank has only hydrogen chloride and auxiliary fuel remaining in the condensed and filtered gaseous oil and gas. In the subsequent processing step, when the filtered gaseous oil and gas treated by the separation step is sent to the vacuum pump via the pipeline, the hydrogen chloride in the filtered gaseous oil and gas is dissolved in water and is stored in the hydrochloric acid storage tank. The remaining auxiliary fuel that is not dissolved in water is stored in the fuel storage tank through a pipeline.

Furthermore, the electronic waste processing apparatus in accordance with the present invention has a power supply device, a vacuum cracking device, a filter device, and a separation device. The vacuum device is electrically connected to the power supply device, and has a vacuum pump, a vacuum chamber, and a high-frequency furnace body. The vacuum chamber is connected to and communicates with the vacuum pump. The high-frequency furnace body is disposed in the vacuum chamber. The filter device is electrically connected to the power supply device, and is connected to and communicates with the high-frequency furnace body of the vacuum cracking device. The separation device is electrically connected to the power supply device, is connected to and communicates with the vacuum pump and the filter device, and has a condensation cylinder, a cooling cylinder, and an oil storage tank.

Other objects, advantages and novel features of the invention will become more apparent from the following detailed description when taken in conjunction with the accompanying drawings.

DETAILED DESCRIPTION OF THE PREFERRED EMBODIMENT

Figure 1:
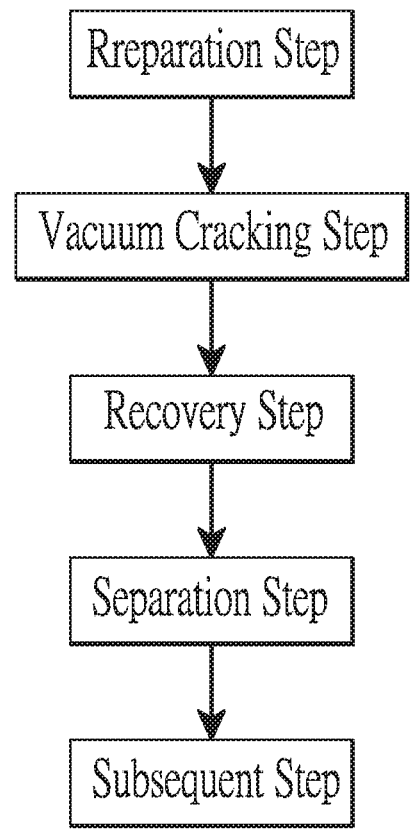
FIG. 1 is a block diagram of an electronic waste processing method in accordance with the present invention.
Figure 2:
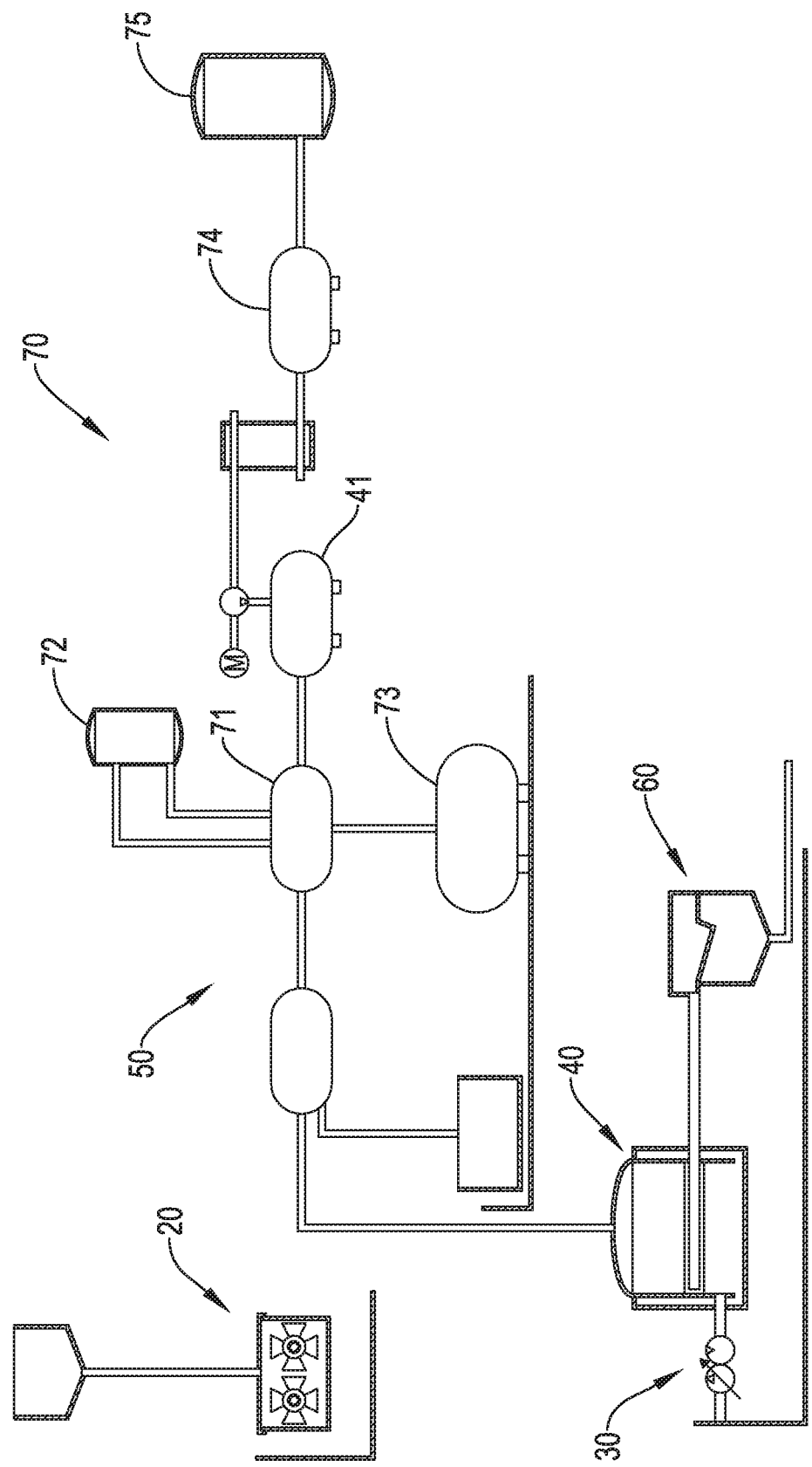
FIG. 2 is a schematic view of an electronic waste processing apparatus in accordance with the present invention.

With reference to FIGS. 1 and 2, an electronic waste processing method in accordance with the present invention comprises a preparation step, a vacuum cracking step, a recovery step, a separation step, and a subsequent processing step.

In the preparation step, with reference to FIG. 2, electronic waste 10, a crusher 20, a power supply device 30, a vacuum cracking device 40, a filter device 50, an electrolysis device 60, and a separation device 70 are prepared. Furthermore, the electronic waste may be abandoned electronic circuit boards, printed circuit boards or transmission lines, etc. The power supply device 30 is electrically connected to the crusher 20, the vacuum cracking device 40, the filter device 50, the electrolysis device 60, and the separation device 70 to allow the above-mentioned devices to operate.

Figure 3:
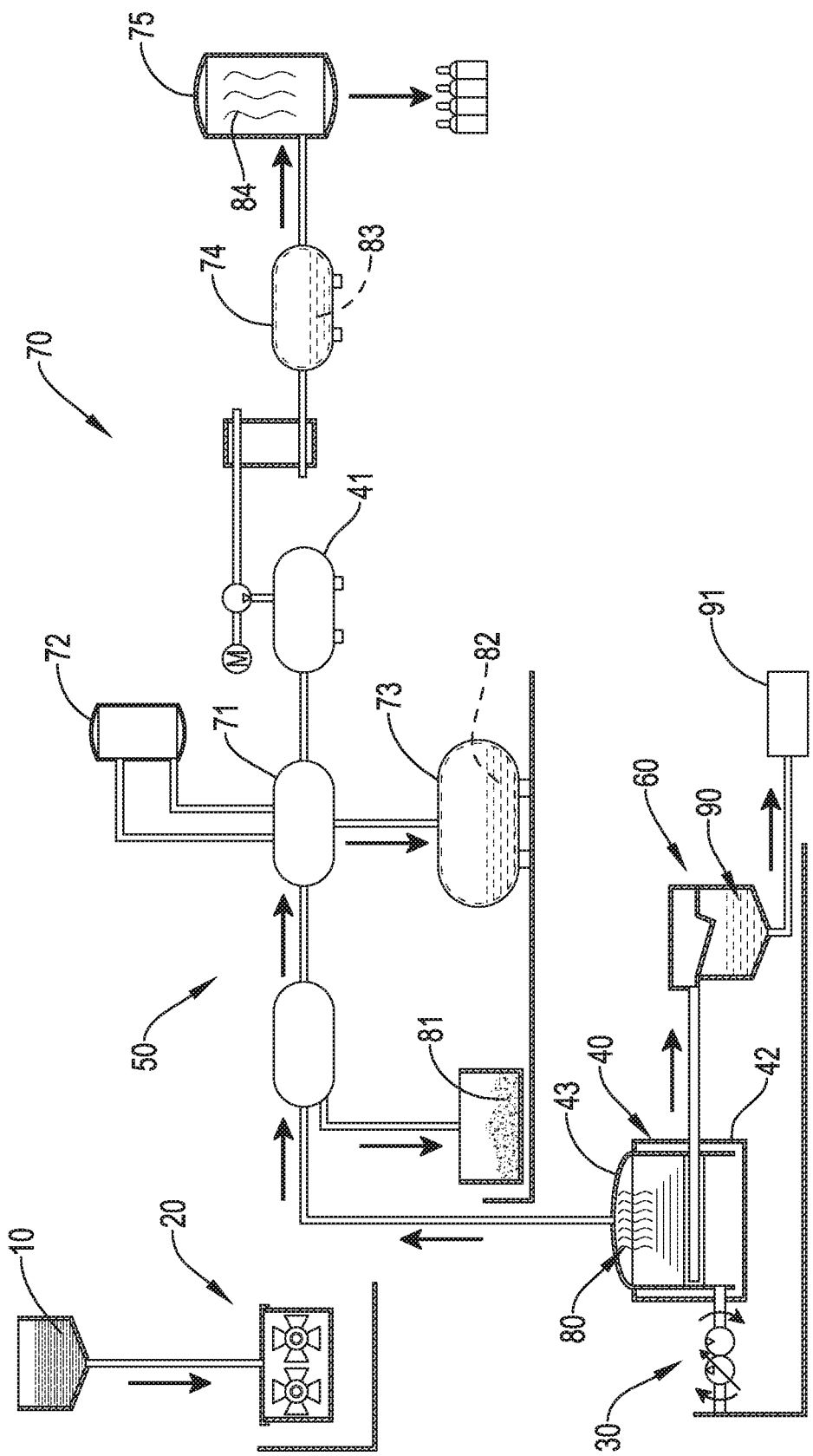
FIG. 3 is an operational side view of the electronic waste processing apparatus in FIG. 2.
Figure 4:
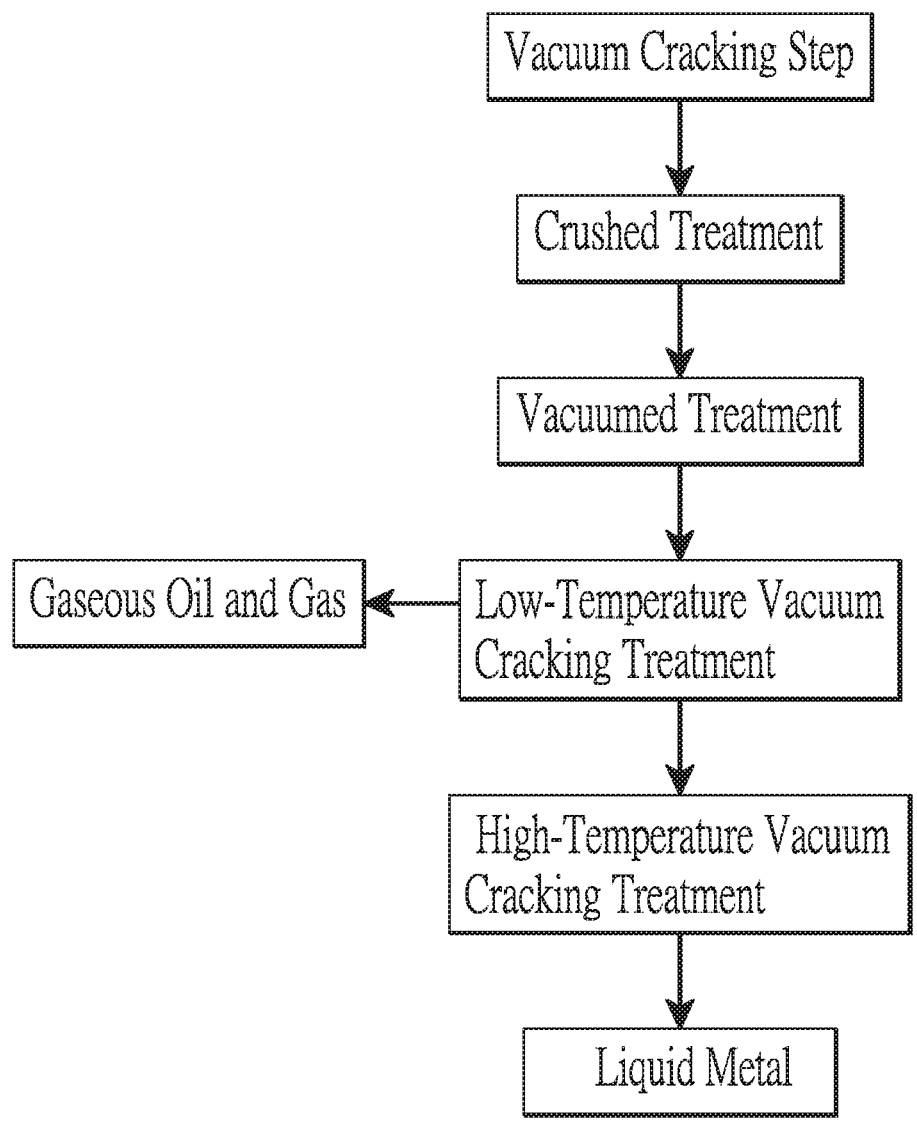
FIG. 4 is an operational side view of a vacuum cracking step of the electronic waste processing method in FIG. 1.

In the vacuum cracking step, with reference to FIGS. 3 and 4, the electronic waste 10 is sent to the crusher 20 and crushed by the crusher 20 to form multiple small pieces. The small pieces of the electronic waste 10 are sent to the vacuum cracking device 40. The vacuum cracking device 40 has a vacuum pump 41, a vacuum chamber 42, and a high-frequency furnace body 43. The vacuum pump 41 is driven by the power supply device 30 and is connected to the vacuum chamber 42, and this enables an interior of the vacuum chamber 42 to be in a vacuum state via the vacuum pump 41 and the power supply device 30. The high-frequency furnace body 43 is disposed in the vacuum chamber 42 and is supplied with power required for high-frequency heating from the power supply device 30.

The high-frequency furnace body 43 is heated to 250° C., so that the plastic materials in each of the small pieces are cracked by low-temperature vacuum cracking and generate gaseous oil and gas 80. Then the remaining metal materials in the small pieces of the electronic waste 10 are heated and melted into liquid metal 90 by vacuum cracking at 1800° C. Furthermore, the electronic waste 10 is sent to the high-frequency furnace body 43 by a cart after the crushing treatment of the crusher 20. Then the vacuum chamber 42 is closed and is vacuumed by the vacuum pump 41. When the interior of the vacuum chamber 42 is vacuumed in the vacuum state, the high-frequency furnace body 43 is operated with two-stage heating for the small pieces of the electronic waste 10. Preferably, the vacuum pump 41 is a water-sealed vacuum pump.

Figure 5:
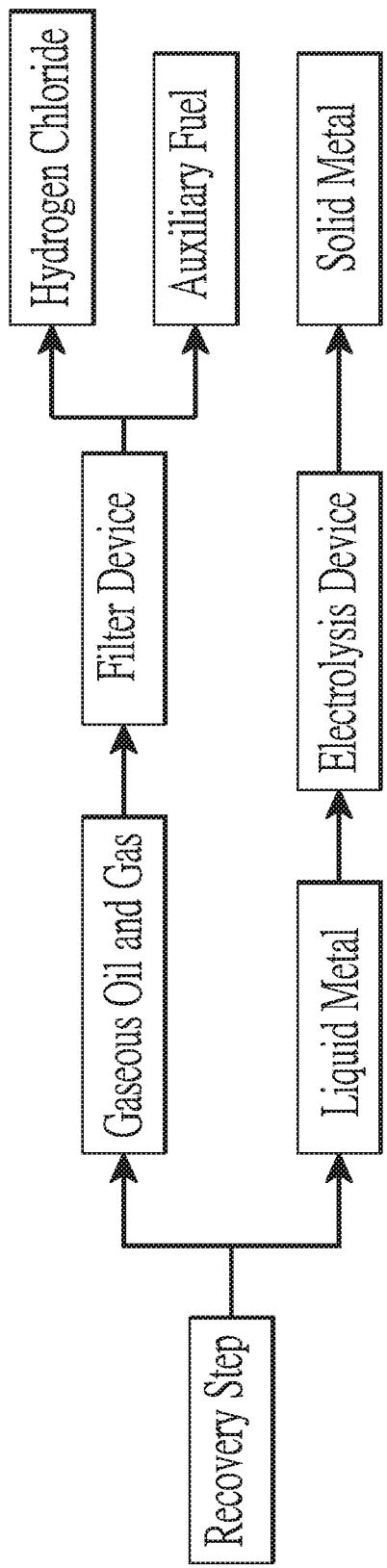
FIG. 5 is an operational side view of a recovery step of the electronic waste processing method in FIG. 1.

In the recovery step, with reference to FIGS. 3 and 5, the gaseous oil and gas 80 and liquid metal 90 are generated in the vacuum cracking step. The gaseous oil and gas 80 generated after a vacuum cracking treatment in the high-frequency furnace 43 is sent to the filter device 50 via a pipeline. After the filtration treatment of the filter device 50, solid slag 81 contained in the gaseous oil and gas 80 is filtered out. The filtered gaseous oil and gas 80 contains hydrogen chloride (HCl) 83 and auxiliary fuel 84 such as gas. The liquid metal 90 is sent to the electrolysis device 60 via another pipeline, and after an electrolysis treatment by the electrolysis device 60, different solid metals 91 such as gold, platinum, silver, copper, tin, etc. are extracted.

Figure 6:
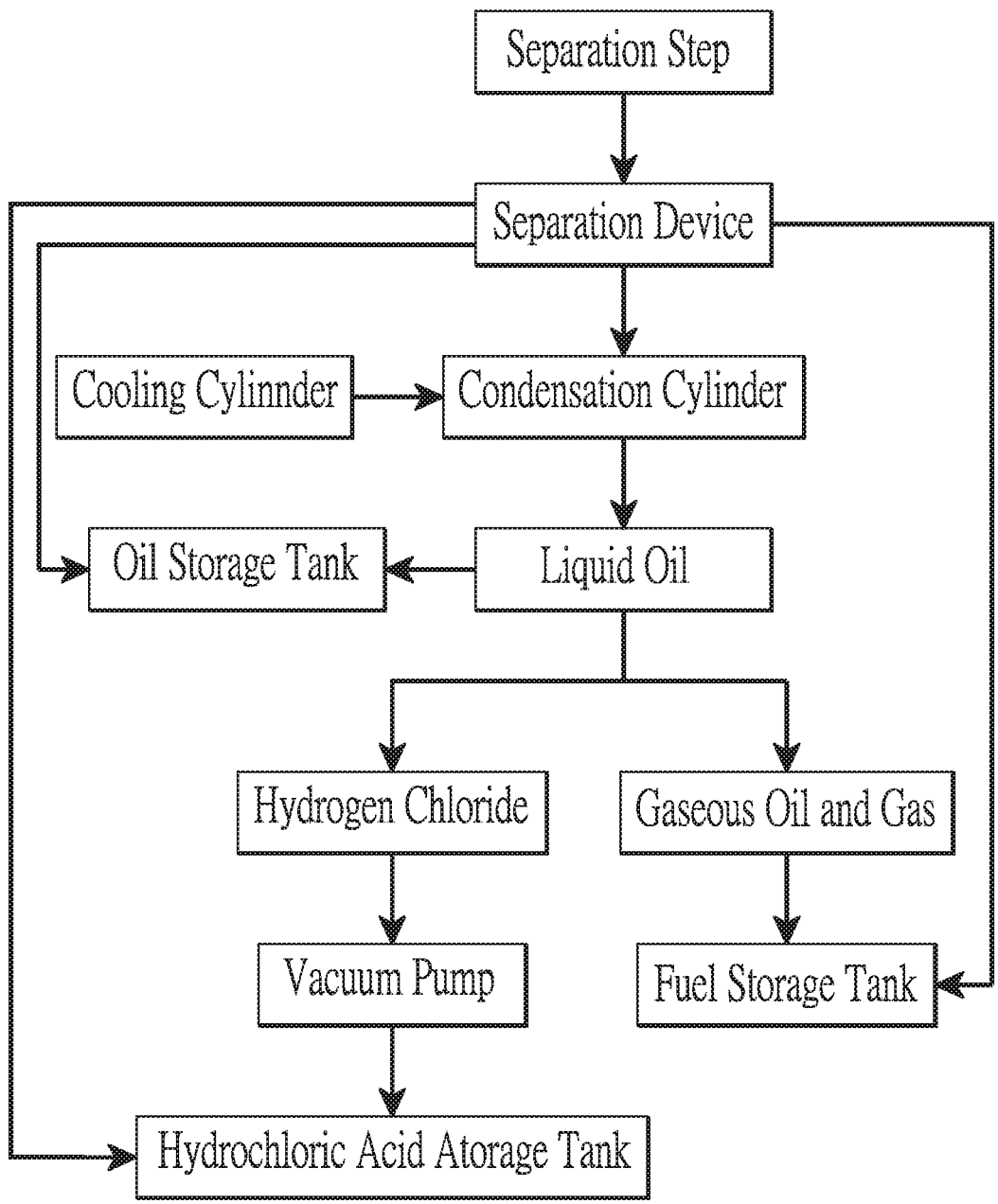
FIG. 6 is an operational side view of a separation step of the electronic waste processing method in FIG. 1.

In the separation step, with reference to FIGS. 3 and 6, the filtered gaseous oil and gas 80 is pipelined to the separation device 70. The separation device 70 has a condensation cylinder 71, an oil storage tank 73, a hydrochloric acid storage tank 74, and a fuel storage tank 75. After the filtered gaseous oil and gas 80 is cooled in the condensation cylinder 71 of the separation device 70, a portion of the filtered gaseous oil and gas 80 generates liquid oil 82 and is stored therein. The oil storage tank 73 has only hydrogen chloride 83 and auxiliary fuel 84 remaining in the condensed and filtered gaseous oil and gas 80.

In the subsequent processing step, with reference to FIG. 3, when the filtered gaseous oil and gas 80 treated by the separation step is sent to the vacuum pump 41 via the pipeline, the hydrogen chloride 83 in the filtered gaseous oil and gas 80 is dissolved in water and is stored in the hydrochloric acid storage tank 74. It can be used as a cleaning or disinfecting method by means of sub-package storage. The remaining auxiliary fuel 84 that is not dissolved in water is stored in the fuel storage tank 75 through a pipeline, and is supplied as a source of fuel or combustion by means of sub-packaging.

With reference to FIGS. 1 and 2, the electronic waste processing method of the present invention is used by an electronic waste processing apparatus, and the electronic waste processing apparatus comprises a power supply device 30, a vacuum cracking device 40, a filter device 50, an electrolysis device 60, and a separation device 70.

The vacuum device 40 is electrically connected to the power supply device 30, and has a vacuum pump 41, a vacuum chamber 42, and a high-frequency furnace body 43. The vacuum chamber 42 is connected to and communicates with the vacuum pump 41. The high-frequency furnace body 43 is disposed in the vacuum chamber 42.

The filter device 50 is electrically connected to the power supply device 30, and is connected to and communicates with the high-frequency furnace body 43 of the vacuum cracking device 40.

The electrolysis device 60 is electrically connected to the power supply device 30, and is connected to and communicates with the high-frequency furnace body 43 of the vacuum cracking device 40.

The separation device 70 is electrically connected to the power supply device 30, is connected to and communicates with the vacuum pump 41 and the filter device 50, and has a condensation cylinder 71, a cooling cylinder 72, and an oil storage tank 73. The cooling cylinder 72 is connected to the condensation cylinder 71 to provide a cooling effect to the condensation cylinder 71. The oil storage tank 73 is connected to and communicates with the condensation cylinder 71.

In addition, the electronic waste processing apparatus further has a crusher 20 connected to the vacuum cracking device 40, and the separation device 70 further has a hydrochloric acid storage tank 74 and a fuel storage tank 75. The hydrochloric acid storage tank 74 is connected to and communicates with the vacuum pump 41. The fuel storage tank 75 is connected to and communicates with the hydrochloric acid storage tank 74.

According to the structural relationship and features of the electronic waste processing method and apparatus thereof of the present invention, when the electronic waste 10 is to be processed, the vacuum cracking apparatus 40 can be supplied with a heating method of different temperatures, respectively for the plastic materials and the metal materials in the electronic waste 10. The cracking and melting avoid the high temperature heating that makes the plastic materials generate toxic gas such as dioxin, and it is relatively unnecessary to provide an air pollution treatment device for treating toxic gas, which can greatly reduce the cost and ensure the health of the field operators and environmental protection.

Furthermore, the method of cracking plastic materials at low temperature can also avoid the gas explosion problem that may occur due to excessive hydrogen chloride concentration. It is relatively safe to use. Furthermore, for gaseous oil and gas 80 and liquid metal 90 after the vacuum cracking step, the liquid oil 82, the liquid hydrogen chloride 83, the gaseous auxiliary fuel 84, and the solid metal 91 are obtained through the recovery step, the separation step, and the subsequent processing step. It may greatly improve the practicability of the electronic waste 10, and provides an electronic waste processing apparatus of safe use and environmental protection, with the electronic waste fully recycled.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An electronic waste processing method comprising:
    a preparation step including:
        preparing electronic waste, a power supply device, a vacuum cracking device, a filter device, and a separation device;
    wherein
    the power supply device is electrically connected to the vacuum cracking device, the filter device, and the separation device;
    the vacuum device has a vacuum pump, a vacuum chamber connected to and communicating with the vacuum pump, and a high-frequency furnace body disposed in the vacuum chamber;
    the separation device is connected to and communicates with the vacuum pump and the filter device, and has a condensation cylinder, a cooling cylinder connected to the condensation cylinder to provide a cooling effect to the condensation cylinder, an oil storage tank connected to and communicating with the condensation cylinder, a hydrochloric acid storage tank, and a fuel storage tank;
    a vacuum cracking step including:
        sending the electronic waste to the vacuum cracking device;
        maintaining a vacuum state in an interior of the vacuum chamber via the vacuum pump that is driven by the power supply device;
        heating plastic materials in the electronic waste by the high-frequency furnace body supplied with power required for high-frequency heating from the power supply device, and cracking the plastic materials in the electronic waste by low-temperature vacuum to generate gaseous oil and gas; and
        heating and melting remaining metal materials in the electronic waste into liquid metal by high-temperature vacuum;
    a recovery step including:
        recovering gaseous oil and gas and liquid metal generated in the vacuum cracking step;
        sending the gaseous oil and gas generated after a vacuum cracking treatment in the high-frequency furnace to the filter device via a pipeline;
        filtering solid slag contained in the gaseous oil and gas out of the gaseous oil and gas by a filtration treatment of the filter device; and
        obtaining hydrogen chloride and auxiliary fuel in the filtered gaseous oil and gas;
    a separation step including:
        pipelining the filtered gaseous oil and gas to the separation device;
        cooling the filtered gaseous oil and gas in the condensation cylinder to generate and store liquid oil therein from a portion of the filtered gaseous oil and gas; and
        keeping the hydrogen chloride and auxiliary fuel in the condensed and filtered gaseous oil and gas; and
    a subsequent processing step including:
        sending the filtered gaseous oil and gas treated by the separation step to the vacuum pump via the pipeline;
        dissolving the hydrogen chloride in the filtered gaseous oil and gas in water to store in the hydrochloric acid storage tank; and
        storing the remaining auxiliary fuel that is not dissolved in water in the fuel storage tank through a pipeline.

2. The electronic waste processing method as claimed in claim 1, wherein
    the preparation step comprises preparing a crusher electrically connected to the power supply device; and
    the vacuum cracking step comprises
        sending the electronic waste to the crusher to be crushed before sending to the vacuum cracking device;
        crushing the electronic waste to form multiple small pieces by the crusher; and
        sending the small pieces of the electronic waste to the vacuum cracking device.

3. The electronic waste processing method as claimed in claim 2, wherein the vacuum cracking step comprises
    sending the electronic waste to the high-frequency furnace body by a cart after the crushing by the crusher;
    closing and vacuuming the vacuum chamber in the vacuum state by the vacuum pump; and
    heating the small pieces of the electronic waste by the high-frequency furnace body with two-stage heating.

4. The electronic waste processing method as claimed in claim 1, wherein the vacuum cracking step includes:
    heating the plastic materials in each of the small pieces of the electronic waste to 250° C. and cracking in low-temperature vacuum to generate the gaseous oil and gas; and
    heating and melting the remaining metal materials in the small pieces of the electronic waste into liquid metal by vacuum cracking at 1800° C.

5. The electronic waste processing method as claimed in claim 2, wherein the vacuum cracking step includes:
    heating the plastic materials in each of the small pieces of the electronic waste to 250° C. and cracking in low-temperature vacuum to generate the gaseous oil and gas; and
    heating and melting the remaining metal materials in the small pieces of the electronic waste into liquid metal by vacuum cracking at 1800° C.

6. The electronic waste processing method as claimed in claim 3, wherein the vacuum cracking step includes:
    heating the plastic materials in each of the small pieces of the electronic waste to 250° C. and cracking in low-temperature vacuum to generate the gaseous oil and gas; and
    heating and melting the remaining metal materials in the small pieces of the electronic waste into liquid metal by vacuum cracking at 1800° C.

7. The electronic waste processing method as claimed in claim 4, wherein
    the preparation step includes:
        preparing a water-sealed vacuum pump as the vacuum pump; and
        preparing an electrolysis device electrically connected to the power supply device; and the recovery step includes:
  sending the liquid metal to the electrolysis device via another pipeline; and
  extracting the liquid metal into different solid metals after an electrolysis treatment by the electrolysis device.

8. The electronic waste processing method as claimed in claim 5, wherein
  the preparation step includes:
    preparing a water-sealed vacuum pump as the vacuum pump; and
    preparing an electrolysis device electrically connected to the power supply device; and
  the recovery step includes:
    sending the liquid metal to the electrolysis device via another pipeline; and
    extracting the liquid metal into different solid metals after an electrolysis treatment by the electrolysis device.

9. The electronic waste processing method as claimed in claim 6, wherein
  the preparation step includes:
    preparing a water-sealed vacuum pump as the vacuum pump; and
    preparing an electrolysis device electrically connected to the power supply device; and
  the recovery step comprises
    sending the liquid metal to the electrolysis device via another pipeline; and
    extracting the liquid metal into different solid metals after an electrolysis treatment by the electrolysis device.

10. The electronic waste processing method as claimed in claim 7, wherein the subsequent processing step comprises
  sub-packaging and storing the hydrogen chloride in the filtered gaseous in the hydrochloric acid storage tank for cleaning or disinfection; and
  sub-packaging the remaining auxiliary fuel in the fuel storage tank for supplying as a source of fuel.

11. The electronic waste processing method as claimed in claim 8, wherein the subsequent processing step comprises
  sub-packaging and storing the hydrogen chloride in the filtered gaseous in the hydrochloric acid storage tank for cleaning or disinfection; and
  sub-packaging the remaining auxiliary fuel in the fuel storage tank for supplying as a source of fuel.

12. The electronic waste processing method as claimed in claim 9, wherein the subsequent processing step comprises
  sub-packaging and storing the hydrogen chloride in the filtered gaseous in the hydrochloric acid storage tank for cleaning or disinfection; and
  sub-packaging the remaining auxiliary fuel in the fuel storage tank for supplying as a source of fuel.

13. The electronic waste processing method as claimed in claim 1, wherein the subsequent processing step comprises
  sub-packaging and storing the hydrogen chloride in the filtered gaseous oil and gas in the hydrochloric acid storage tank for cleaning or disinfection; and
  sub-packaging the remaining auxiliary fuel in the fuel storage tank for supplying as a source of fuel.

14. The electronic waste processing method as claimed in claim 2, wherein the subsequent processing step comprises
  sub-packaging and storing the hydrogen chloride in the filtered gaseous oil and gas in the hydrochloric acid storage tank for cleaning or disinfection; and
  sub-packaging the remaining auxiliary fuel in the fuel storage tank for supplying as a source of fuel.

15. The electronic waste processing method as claimed in claim 3, wherein the subsequent processing step comprises
  sub-packaging and storing the hydrogen chloride in the filtered gaseous oil and gas in the hydrochloric acid storage tank for cleaning or disinfection; and
  sub-packaging the remaining auxiliary fuel in the fuel storage tank for supplying as a source of fuel.

16. An electronic waste processing apparatus comprising:
  a power supply device;
  a vacuum cracking device electrically connected to the power supply device, and having
    a vacuum pump;
    a vacuum chamber connected to and communicating with the vacuum pump; and
    a high-frequency furnace body disposed in the vacuum chamber;
  a filter device electrically connected to the power supply device, and connected to and communicating with the high-frequency furnace body of the vacuum cracking device; and
  a separation device electrically connected to the power supply device, connected to and communicating with the vacuum pump and the filter device, and having
    a condensation cylinder;
    a cooling cylinder connected to the condensation cylinder to provide a cooling effect to the condensation cylinder; and
    an oil storage tank connected to and communicating with the condensation cylinder.

17. The electronic waste processing apparatus as claimed in claim 16, wherein the electronic waste processing apparatus has a crusher connected to the vacuum cracking device.

18. The electronic waste processing apparatus as claimed in claim 16, wherein the separation device has
  a hydrochloric acid storage tank connected to and communicating with the vacuum pump; and
  a fuel storage tank connected to and communicating with the hydrochloric acid storage tank.

19. The electronic waste processing apparatus as claimed in claim 17, wherein the separation device has
  a hydrochloric acid storage tank connected to and communicating with the vacuum pump; and
  a fuel storage tank connected to and communicating with the hydrochloric acid storage tank.

20. The electronic waste processing apparatus as claimed in claim 18, wherein the electronic waste processing apparatus has an electrolysis device electrically connected to the power supply device, and connected to and communicating with the high-frequency furnace body of the vacuum cracking device.

* * * * *